United States Patent [19]
Curley et al.

[11] Patent Number: 5,954,659
[45] Date of Patent: Sep. 21, 1999

[54] METHOD AND APPARATUS FOR INVASIVELY MEASURING CARDIAC OUTPUT BY DETECTING TEMPERATURE DIFFERENCES OF BLOOD HEATED BY RADIATION

[76] Inventors: Michael G. Curley, 430 Huron Ave., Cambridge, Mass. 02138; William H. Newman, 507 NW. 22nd Ave, Apt. 305, Portland, Oreg. 97210

[21] Appl. No.: 08/602,916

[22] Filed: Feb. 16, 1996

[51] Int. Cl.[6] ............................ A61B 5/027; A61B 5/028; A61B 5/026
[52] U.S. Cl. .............................................. 600/505; 600/504
[58] Field of Search ........................................ 128/691, 692, 128/69.5, 664–667; 600/504, 505, 508, 473, 474, 476, 477, 479, 480

[56] References Cited

U.S. PATENT DOCUMENTS

| | | |
|---|---|---|
| 3,527,542 | 9/1970 | Penhasi et al. . |
| 4,015,593 | 4/1977 | Elings et al. . |
| 4,236,527 | 12/1980 | Newbower et al. ..................... 128/692 |
| 4,321,918 | 3/1982 | Clark, II . |
| 4,507,974 | 4/1985 | Yelderman . |
| 4,576,182 | 3/1986 | Normann . |
| 4,614,514 | 9/1986 | Carr et al. . |
| 4,621,929 | 11/1986 | Phillips . |
| 4,632,125 | 12/1986 | Webler et al. . |
| 4,721,115 | 1/1988 | Owens . |
| 4,785,823 | 11/1988 | Eggers et al. ........................... 128/692 |
| 4,839,142 | 6/1989 | Charm . |
| 4,975,246 | 12/1990 | Charm . |
| 5,073,167 | 12/1991 | Carr et al. . |
| 5,344,435 | 9/1994 | Turner et al. . |
| 5,357,967 | 10/1994 | Dixon et al. ............................ 128/691 |
| 5,389,335 | 2/1995 | Charm et al. . |
| 5,634,470 | 6/1997 | Norris . |
| 5,692,514 | 12/1997 | Bowman ................................. 600/504 |

FOREIGN PATENT DOCUMENTS

| | | | |
|---|---|---|---|
| 459480 | 12/1991 | European Pat. Off. ............... | 128/691 |
| 3817603 A1 | 5/1988 | Germany . | |

OTHER PUBLICATIONS

Trautman, E.D.; Newbower, R.S., "Cardiac Output, Thermodilution Measurement of," *Encyclopedia of Medical Devices and Instrumentation*, J.E. Webster, Ed., Wiley, New York.

Trautman, E.D.; Newbower, R.S., "The Development of Indicator–Dilution Techniques," *IEEE Transactions on Biomedical Engineering*, vol. BME–31, No. 122, Dec. 1984.

Normann, R.A.; Johnson, R.W.; Messinger, J.E.; Sohrab, B., "A Continuous Cardiac Output Computer Based on Thermodilution Principles," *Annals of Biomedical Engineering*, vol. 17, pp. 61–73, 1989.

Charm, S.E.; Landau, S.H., "Thermalizer—High–Temperature Short–Time Sterilization of Heat–Sensitive Biological Materials," *Annals New York Academy of Sciences*, pp. 608–612.

*Primary Examiner*—William E. Kamm
*Assistant Examiner*—Carl H. Layno
*Attorney, Agent, or Firm*—Cesari and McKenna LLP

[57] ABSTRACT

A cardiac output measurement device volumetrically heating a predefined quantity of blood flowing through a heart by arbitrarily applying a containable energy field to the blood using a thermodilution catheter having an emitter that uniformly emits electromagnetic radiation. Blood temperature is measured at the pulmonary artery by a sensor that provides a signal representing the temperature of the mixed blood to a controller. The controller determines the flow rate, or cardiac output, by performing a heat balance analysis based upon the applied power and resultant blood temperature. The cardiac output measurement device includes a catheter having an emitter and, preferably, a temperature sensor located at its distal end. The catheter is coupled to a laser or other energy source capable of generating containable electromagnetic radiation, such as an ultraviolet or microwave energy source. Significantly, for the preferred laser source, the emitter is a diffuser that uniformly emits the laser-generated energy into a predetermined volume of flowing blood. A temperature measuring system of the controller receives temperature signals from the sensor and generates a resultant temporal temperature profile used by a flow estimator to determine the flow rate and generate a power excitation function to control the energy source. The resultant measured flow may also be presented though a user interface.

37 Claims, 6 Drawing Sheets

METHOD AND APPARATUS FOR INVASIVELY MEASURING CARDIAC OUTPUT BY DETECTING TEMPERATURE DIFFERENCES OF BLOOD HEATED BY RADIATION

BACKGROUND OF THE INVENTION

1. Field of the Invention

The present invention relates generally to the measurement of cardiac output and, more particularly, to thermodilution cardiac output measurement techniques.

2. Description of the Related Art

Cardiac output, conventionally defined as the amount of blood pumped by the heart over several cardiac cycles, is a fundamental performance measurement for assessing the condition of the heart. For example, cardiac output is routinely measured as part of diagnostic cardiography and patient monitoring.

Physicians' concern with cardiac output generally relates to the output of the left heart, which supplies the body with oxygenated blood. Since the output of the two halves of the heart are equal, cardiac output can be measured on either side of the heart. However, left heart measurements are much more difficult and dangerous than right heart measurements. In a left heart measurement, the catheter must be threaded into the heart via an artery, against the direction of blood flow, into the left ventricle and finally into the left atrium. Bleeding, infection, and other complications are common risks. By contrast, the measurement of right heart output is considerably safer and easier to perform, particularly because the catheter is threaded through the venous system. Consequently, cardiac output is most often determined by performing right heart measurements.

The technique currently accepted by the clinical community to measure cardiac output is known as the "bolus thermodilution" measurement technique. A measurement catheter is threaded through a vein in either the thigh or the shoulder until the tip of the catheter, containing a thermistor (an electrical temperature sensor), is located in the pulmonary artery, and a fluid ejection port of the catheter is located in the right atrium of the heart. To make a measurement, the administering clinician injects a small quantity (approximately 10 cc) of cold saline solution through the catheter into the right atrium via the port. The cold saline solution mixes with the blood in the right atrium and ventricle, and the mixture is ejected by the heart into the pulmonary artery. The mixing of cold solution with the blood cools the blood temperature by 0.5 to 1 degree Celsius, an effect that dissipates over the next several heartbeats, depending on the flow rate. The thermistor measures the temperature of the mixture as the cooled blood is ejected from the heart over the next few heartbeats. An energy balance equation is then used to calculate the average flow from the temperature-time data.

While conceptually simple, this technique has several drawbacks. Due to various sources of measurement noise, any one cardiac output measurement has a high level of uncertainty. As a result, from 3 to 6 repetitions are required to establish confidence in the reading. The total fluid load resulting from these repetitions can be harmful to the patient. Accordingly, the measurements are intermittently performed, with the approximate maximum being one set of 3–6 repetitive measurements per hour. This periodic performance of the test prevents this technique from providing the clinician with continuous cardiac output measurements.

Furthermore, the measurements are labor-intensive: an operator's intervention is required to make each fluid injection. As a result, the measurements are operator-dependent, and vary according to the "injection technique" of the administering clinician. Finally, there are additional sources of measurement error, including errors due to the warming of the saline in the cooled container and in the catheter prior to and during injection. Furthermore, natural variations in the nominal blood temperature, typically approximately 10 millidegrees, introduce additional measurement errors.

Techniques proposed to overcome these shortcomings have generally consisted of replacing the injection of chilled solution with a small heater on the surface of the catheter to cause a localized temperature change in the blood. An example of this approach is described in U.S. Pat. No. 4,576,182 to Normann (hereinafter "Normann"). In Normann, a catheter with an electrically-resistive heating element wound around its outer surface is heated by the discharge of a capacitor through the heating element. Although this technique permits automatic and rapid measurements while eliminating fluid overload and operator-induced variation problems associated with the use of chilled saline solution, there are a number of drawbacks which make this approach impractical.

Specifically, although the blood cells sustain the cooling caused by the injection of saline with no damage, they are very susceptible to damage caused by increases in temperature. Heat enters the blood by conduction from the surface of the catheter to the relatively cool flowing blood. The maximum temperature in the blood thus occurs at the catheter/blood interface. To deliver sufficient heat to the blood to obtain a reliable temperature signal may require a relatively high temperature at the interface, such as to damage blood cells adjacent to the heater. This problem is exacerbated when the resistive heating element directly contacts the blood.

In fact, the Underwriter's Laboratory standard for Medical Electronics, UL544, limits contact temperature of medical devices to 41 degrees Celsius. Similar limits are imposed by IEC standards in the international community. Heat transfer considerations therefore limit the power delivered to the blood using standard size catheters to less than 10 watts. This limitation on the power levels of the resistive heaters severely reduces the signal-to-noise ratio for this technique, which in turn reduces its accuracy. The reduction in signal strength is best illustrated by comparing this power to the saline injection technique, wherein a 10 cc, 0 degree Celsius saline injection over 2 seconds is equivalent to the removal of 750 watts of power from the blood.

Another prior approach, described in U.S. Pat. No. 4,621,929 to Phillips (hereinafter "Phillips"), uses anemometric techniques to heat and measure fluid flow. In Phillips, various external energy sources are used to excite and heat an absorber within the catheter to serve as the heat source within the fluid. This technique, however, also relies on conduction of this energy into the fluid, and thus has limitations on the total power similar to the resistive thermal heater approach described above.

Phillips also describes the use of laser energy to directly heat the blood in conjunction with various methods of determining flow rates. In such a method constant-power heating is used, with the flow rate determined by measuring the temperature increment downstream. In another Phillips method, the laser power is adjusted to maintain a constant temperature increment downstream, in which case the flow is determined by measuring the power required to maintain the constant temperature. These latter techniques suffer from two conflicting problems.

First, the analysis method implemented in Phillips requires that steady state thermal conditions be achieved prior to taking readings. This in turn requires that the blood be heated for a sufficiently long period of time. However, the continuous heating of blood to perform these measurements can add significantly to normal basal energy production and can cause the patient to overheat. As a result, Phillips must restrict the power to such a degree that the benefit of directly heating the blood is lost.

Second, the technique itself will cause an increase in the baseline blood temperature, which will necessitate numerous cessations in the heating to monitor this temperature drift. In order to monitor the baseline temperature of the blood, Phillips cycles the heater power, waiting for the temperature increments to decay, and then measuring the temperature to establish the new baseline. Once it is measured, power is reapplied to the heater. Thus, this approach necessitates numerous cessations in the heating to monitor this temperature drift, which prevents the achievement of the steady state temperature levels necessary to make temperature measurements.

Another conventional approach, described in U.S. Pat. No. 4,785,823 to Eggars et al. (hereinafter "Eggars"), applies a high-frequency electric potential difference to electrodes in the catheter to generate a current though the blood to create a bolus of blood at an elevated temperature. There are significant drawbacks to this approach, however.

First, the heating is directly dependent on the current density, which is significantly higher near the electrodes than at a distance away from the electrodes. Thus, the resulting heating field is not uniform, with the blood immediately adjacent to the electrodes reaching a higher temperature than the majority of the blood located at a distance from the electrodes. In addition to the nonuniform heating of the blood, this also results in damage to the blood cells adjacent to the electrodes or limits the power to such a degree that signal reliability is reduced.

Another problem with the Eggars approach is that the current field for reasonable resistance values spreads out fairly far into the blood, resulting in a non-containable energy field. To obtain a desirable energy transfer, electrodes having a resistance of approximately 50 ohms are preferred. This requires a significant electrode spacing which will likely result in the current entering the heart wall. The inevitable loss of energy into the heart wall violates the energy balance on which this measurement is based, and thus renders the measurement inaccurate.

Another problem with the Eggars approach is that the resistance between the electrodes is a function of the distance between them. The resistance in turn, affects the power transferred to the blood. There will be relative movement of the electrodes due to the bending of the catheter during use, causing the spacing between the electrodes to change. This will alter the resistance between the electrodes, thereby altering the power that will be delivered to the blood. This leads to further measurement inaccuracies.

What is needed, therefore, is a means for measuring cardiac output that enables essentially continuous measurement with a sufficiently high energy transfer while simultaneously minimizing the heat load experienced by the patient. Such a measurement system must be capable of responding to natural variations in the baseline blood temperature and allow flexible heating and analysis techniques to minimize the effect of thermal noise in the blood on the measurement of the flow rate.

SUMMARY OF THE INVENTION

The present invention is a cardiac output measurement device for volumetrically heating a predefined quantity of blood flowing through a heart by arbitrarily applying a containable energy field to the blood using a thermodilution catheter having an emitter that uniformly emits electromagnetic radiation or ultrasound energy into the surrounding blood, where it is absorbed and converted into heat. Thus, the heat is generated throughout a fairly well-defined volume of the blood instead of being conducted into the blood from a heated interface. Substantially more heat can therefore be dissipated in the blood without incurring the disadvantage of a localized temperature excess.

Blood temperature is measured in the pulmonary artery by a sensor that provides a signal representing the temperature of the mixed blood to a controller. The controller determines the flow rate, or cardiac output, by performing a heat balance analysis based upon the applied power and resultant blood temperature. A temperature measuring unit of the controller receives temperature signals from the sensor and generates a resultant temporal temperature profile used by a flow estimator to determine the flow rate and generate a power excitation function to control the energy source. The resultant measured flow may also be presented though a user interface.

Significantly, the ability to accurately deliver a large amount of energy to a predefined volume of blood during selectable time periods enables the present invention to implement sophisticated heating and data analysis protocols to achieve continuous, reliable, and accurate cardiac output measurements while not exceeding safe thermal limits that may damage the blood cells or overheat the patient. Specifically, the volumetric heating of the blood enables the present invention to deliver significantly greater power to the blood, resulting in a considerably larger signal-to-noise ratio than heretofore achieved. Moreover, the heat is preferably applied in a predetermined temporal pattern, with analysis techniques being used with the downstream temperature sensor. This reduces the effects of changes in baseline blood temperature and thermal noise.

Advantageously, the energy source of the present invention generates a containable energy field that is significantly less susceptible to undesirable alterations and can be accurately applied to a predefined volume of blood and not the heart wall. Furthermore, such a definable energy field is controllable and may easily be adapted to different blood and other fluid systems.

Other advantages of the present invention include the ability to provide essentially continuous measurement of cardiac output, providing a sufficient amount of data to the clinician in a relatively short period of time; its insensitivity to the techniques of the individual applying the procedure, and reduced labor requirements with the associated cost savings.

Further features and advantages of the present invention as well as the structure and operation of various embodiments of the present invention are described in detail below with reference to the accompanying drawings. In the drawings, like reference numbers indicate identical or functionally similar elements. Additionally, the left-most digit of a reference number identifies the drawing in which the reference number first appears.

BRIEF DESCRIPTION OF THE DRAWINGS

For a fuller understanding of the nature of the invention, reference should be made to the following detailed description taken in connection with the accompanying drawings, in which.

DESCRIPTION OF THE INVENTION

Figure 1:
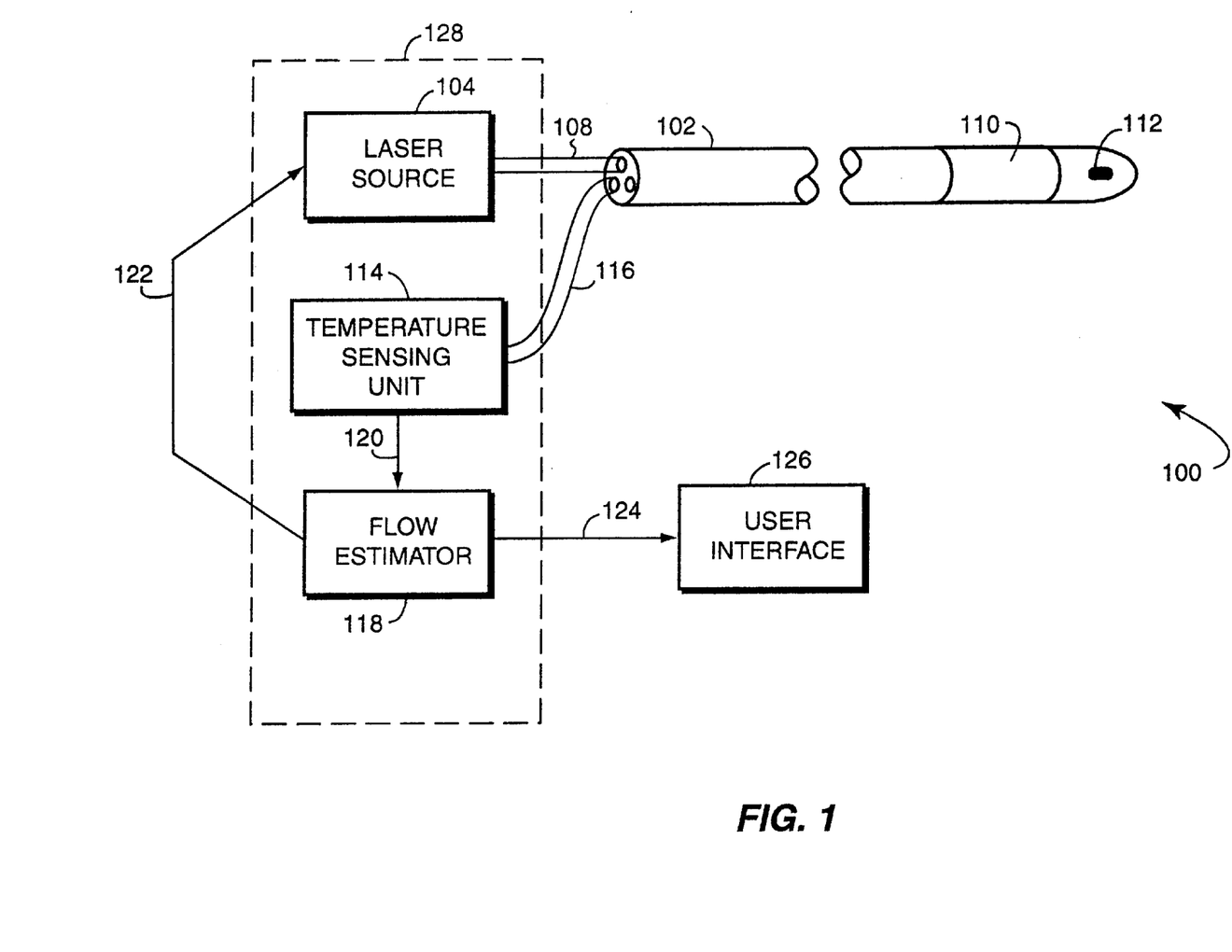
FIG. 1 is a schematic block diagram of the preferred embodiment of the cardiac output measurement system of the present invention.

FIG. 1 illustrates a preferred embodiment of the cardiac output measurement system 100 of the present invention. The system 100 includes a catheter 102 having an emitter 110 for emitting electromagnetic radiation, and a temperature sensor 112 located at its distal end. The catheter 102 is coupled to a laser source 104 via an optical fiber 108 and to a temperature sensing unit 114 via signal lines 116. The system 100 further includes a flow estimator 118 for analyzing a downstream resultant temperature profile provided by the temperature sensing unit 114 through a communication path 120, and for controlling the laser source 104 by providing a predetermined power excitation function to the laser source through a communication path 122.

The measured flow rate is determined by the flow estimator 118 based upon the applied power and the resultant temperature profile. An indication of the flow rate may be presented to an optional user interface 126 through communication path 124. Furthermore, the flow estimator 118 may be configured to receive information from the administering clinician related to the heating and analysis protocols.

Figure 2:
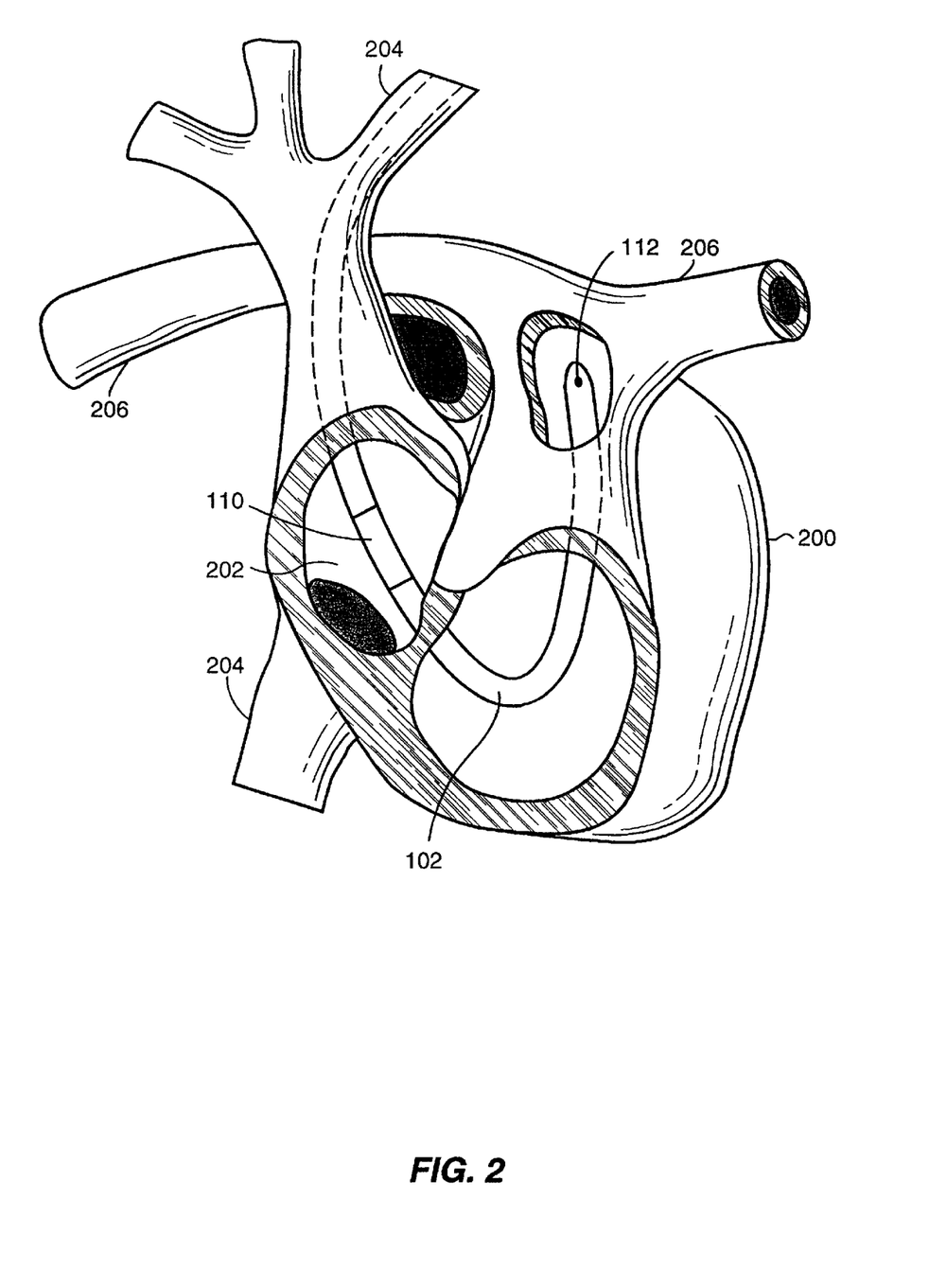
FIG. 2 is a partially cut-away perspective view of the human heart with the catheter of the cardiac output measurement system of the present invention finally positioned in the right atrium and pulmonary artery to make cardiac output measurements.

FIG. 2 illustrates the preferable position of the catheter 102 in a human heart 200 to make cardiac output measurements. The catheter is inserted into the right atrium 202 of the heart through the venous system 204 and is placed such that the emitter 110 is in or near the right atrium and the downstream temperature sensor 112 is placed such that it protrudes into the pulmonary artery 206. The procedure for placing the catheter 102 into the heart as shown in FIG. 2 is well known in the art.

As will become evident from the following description, the present invention may be adapted to determine the flow rate of any fluid in any single-input, single-output flow system, such as other portions of the circulatory system (e.g., arteries), as well as in industrial applications. For ease of description, the operation of the cardiac output measurement system 100, and the functions performed by its integral components introduced above, will be described below with reference to fluid flow in a tube.

Figure 3:
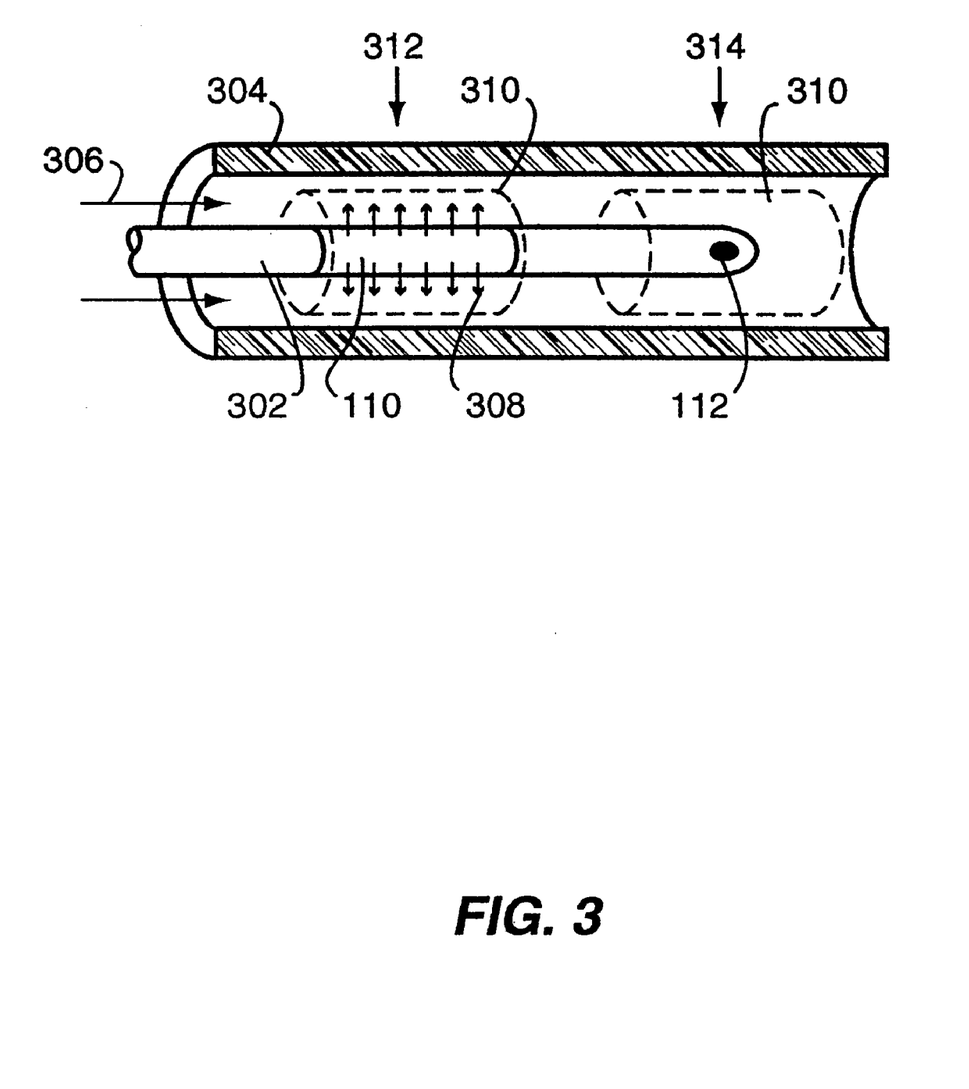
FIG. 3 is an isometric view of an elongate member of a flow rate system of the present invention inserted into a tube through which a fluid is flowing.

FIG. 3 shows an elongated member 302 inserted into a tube 304 through which a fluid 306 is flowing. In the preferred embodiment wherein the energy source 104 is a laser source, the laser light 308 is emitted at the emitter 110 which is, preferably, a diffuser. The diffuser emits laser energy to heat a predefined volume 310 of the fluid surrounding the elongate member 302 at location 312. At some time later, the heated volume of fluid 310 will have been convected downstream to a location 314 over the temperature sensitive element 112. The sensor 112 will respond to the fluid volume 310 passing over it and, specifically, will register an increase in temperature in the temperature measurement unit 114.

In one form of the invention, the diffuser may essentially constitute the surface of the elongated member for some length. In another form, the diffuser may be encapsulated by a material that is essentially transparent at the frequency of laser light that will be used to heat the fluid (discussed below). In either case, the laser energy emerging from the diffuser is substantially uniform across the length and around the circumference of the diffuser, providing an essentially uniform distribution of electromagnetic energy which is almost wholly absorbed by a predetermined volume of the fluid. In the preferred embodiment, diffuser 110 is a Lightstic model diffuser, available from Rare Earth Medical, Yarmouth, Mass., USA. However, as would be apparent to those skilled in the art, other means of emitting the laser energy may be used.

The volumetric heating of the blood to serve as the thermal indicator allows a transfer of more power into the blood without exceeding safe temperature limits for the blood, particularly at the blood-catheter interface. Thus, the resulting temperature signal generated by sensor 112 will be greater than that provided by resistive heaters and thus less susceptible to the effect of thermal noise within the blood, thereby significantly increasing the accuracy of the measurement.

In addition, the fluid need not have a velocity that is substantially constant over time or over location within the tube for the efficient and uniform heating of the fluid. It should also be noted that the present invention is significantly less susceptible to undesirable alterations than presently known methods. For example, if the catheter and/or laser diffuser slightly bends when inside the right atrium, it will not substantially change the emitted energy field.

The power of the laser and the wavelength of the laser light should be chosen such that the light energy is essentially completely absorbed within the fluid and not appreciably absorbed by the tube wall. That is, the laser energy preferably penetrates relatively deeply into the fluid 306 to heat the maximum volume of fluid, but little of the energy reaches the wall. Any absorption by the wall of the tube adversely affects the flow rate analysis (discussed below).

Referring to FIG. 2, in the preferred application as a cardiac output measurement system, the emitter 110 is preferably located in the right atrium 202. Typically, the mean diameter of the right atrium is 3.7 centimeters, with a range of 2.5–4.9 centimeters. For the laser energy to penetrate relatively deeply into the blood while not penetrating the walls of the heart 200, the laser light has a preferred wavelength of approximately 980 nanometers, yielding a penetration depth of about 2.5 millimeters. The preferred range of wavelength is 800–1000 nanometers due to the above variations in atrium diameter. Given the mean diameter of the right atrium, a decay length of 3 millimeters or less for the absorbed power will ensure that the energy will heat only the blood. Thus, a volumetrically-heated bolus of blood is heated while essentially all the emitted energy is absorbed by the blood and not by the cardiac wall.

Although penetration of the wall adversely affects flow rate measurements, it is not a requirement that there be no loss of energy in the laser fiber 108, diffuser 110, or any coating that may be placed over the diffuser. Any energy lost within the fiber 108 or the connections between the fiber and the laser source 104 can be compensated for by measuring the transmission efficiency of the laser source/fiber combination, using methods known to those skilled in the art.

Since the diffuser 110 is not a perfectly efficient light transmitter, a small percentage of the energy will be lost in the diffuser itself and the surrounding coating, if any. The resulting heat will be conducted into the fluid and will add to the heat caused by the uniform absorption of laser energy. This slight conductive heating of the blood is insufficient to raise the blood temperature to an excessive level at the blood-diffuser interface. Furthermore, this conductive heating does not affect the accuracy of the temperature measurement since the temperature sensed downstream at the sensor 112 does not distinguish between conductively-heated and volumetrically-heated blood.

The distance between the emitter 110 and the thermistor 112 should be such that the blood has a sufficient opportunity to mix because, despite the improved volumetric heat distribution provided by the invention, not all of the blood will be subject to the electromagnetic radiation. Thus, some mixing of the fluid should occur prior to temperature sensing. However, the distance should not be so great that significant heat is lost through the walls of the tube, since, as noted above, such absorption adversely affects the measurement accuracy.

Referring to FIG. 2, in the preferred application as a cardiac output measurement system, a distance of approximately 20 cm between the emitter 110 and sensor 112 is preferred. As the heated volume of blood travels that distance, the warm blood mixes with the relatively cool blood prior to reaching the sensor 112. At this distance there is minimal heat transferred into the walls of the heart 200 and pulmonary artery 206; the losses that are experienced lead to minor and tolerable inaccuracies. The optimal distance between the emitter and the temperature sensor is dependent upon various factors. For example, the anticipated flow rate, the amount of mixing that occurs within the fluid, and the ability of the fluid to retain as well as conduct heat, are considerations in determining the distance between the emitter and the sensor.

In the preferred embodiment of the present invention, the source of electromagnetic radiation is laser source 104. Preferably, the laser source 104 is a diode laser, available from Spectra Diode Laser (SDL), San Jose, Calif., USA. However, as would be apparent to those skilled in the art, other types of laser sources may be implemented in the present invention.

In the preferred embodiment of the invention, temperature sensor 112 is a thermistor that will not excessively self-heat (causing artificial temperature rise) and will have a sufficiently fast time constant for the chosen application. However, as those skilled in the art would find apparent, other commercially available temperature-sensitive elements, such as thermocouples or diodes may be used.

Figure 4:
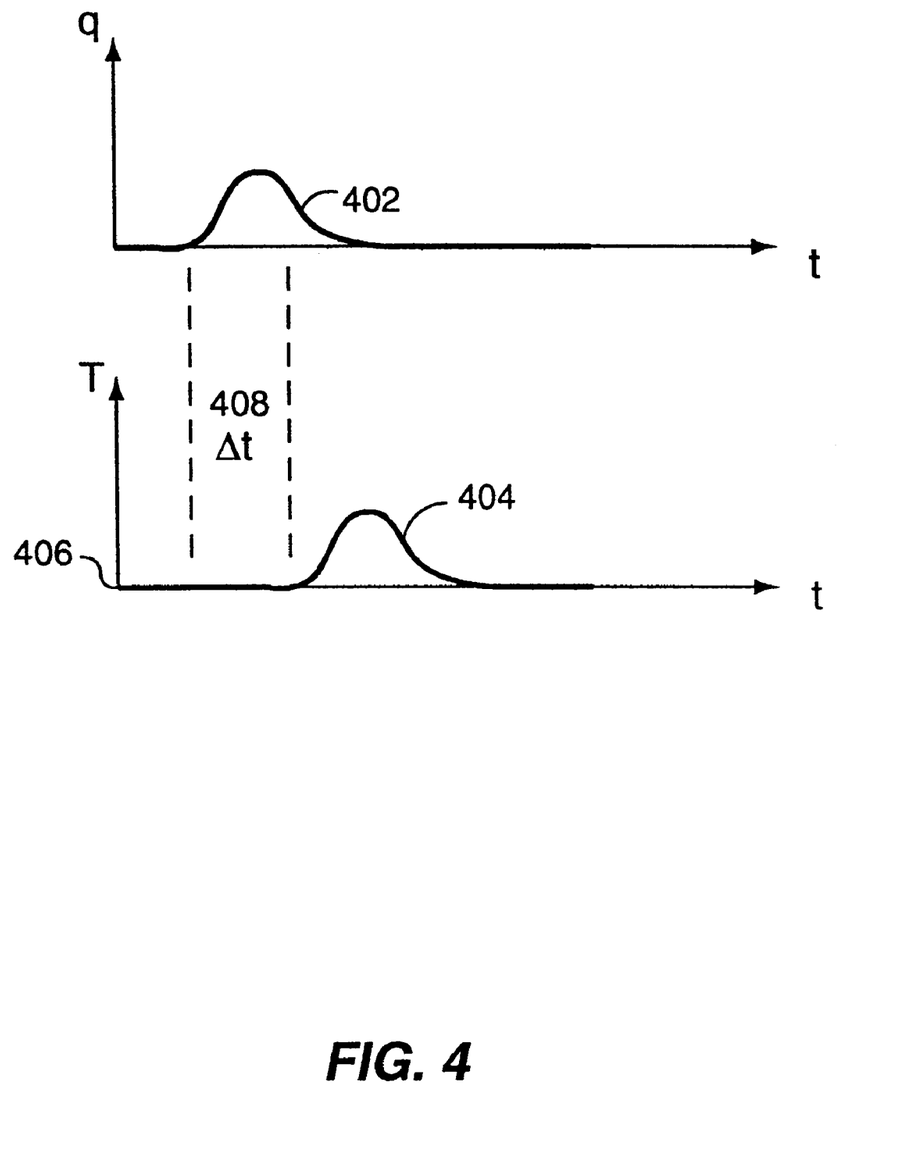
FIG. 4 is an exemplary excitation function and a resultant temperature profile generated by the cardiac output measurement system of the present invention.

As noted, the system 100 further includes a flow estimator that produces the energy excitation function and applies analysis techniques to determine the flow rate based upon the output of the temperature sensing unit. FIG. 4 shows one example of an excitation function 402 and temperature sensed at sensor 112. The central flow estimator 118 excites the laser source 104 such that it generates power q(t) 402. The energy from the laser source 104 is transmitted to the diffuser 110 through the fiber conduit 108 and is then transmitted into the fluid, where it is absorbed and converted to thermal energy as described above.

At some time (delta t) 408 later, the temperature measured by the temperature sensitive element 112 and the temperature sensing unit 114 increases above the baseline temperature of the fluid, $T_{baseline}$ 406, with a response function T(t) 404. The baseline temperature is the temperature of the fluid when energy is not applied to the fluid. The baseline temperature can change over time, sometimes referred to as drift, due to unavoidable changes in the fluid temperature or by recirculation of the fluid, previously heated by application of energy to the fluid, back into the inlet of the tube in which the measurement is being made.

Flow rate is estimated from these functions by performing a heat balance on the input power and the resultant fluid temperature. This method is commonly used in the bolus thermodilution (saline solution injection) technique described above, and is further described in U.S. Pat. No. 4,576,182 to Normann, herein incorporated by reference in its entirety. The volumetric flow rate, in units of m³/sec, following injection of a pulse of heat into the fluid is governed by the equation:

$$\text{Flow} = \frac{\int_0^\infty q(t)dt}{\rho_f c_f \int_0^\infty (T(t) - T_{Baseline})dt}$$

wherein q(t) is the applied power (Watts),
$e_f$ is the density of the blood (Kg/m³),
$c_b$ is the specific heat of the blood (Joules/Kg °K),
T(t) is the measured temperature at time t (°K), and
$T_{Baseline}$ is the baseline temperature (°K).

While the above expression indicates that the integrals are calculated for all time, in reality the time limits are finite, and, for the numerator, the integral includes only those times that the applied power is greater than zero. This enables the flow estimator to base its flow rate determination on specific instances of volumetric heating. This provides the present invention with flexibility in selecting the manner in which the radiation is delivered to the fluid. This is particularly important in the preferred application of cardiac output measurement. One method of choosing the integration limits for the temperature is described by Normann et al., in the Annals of Biomedical Engineering, volume 17, pages 61–73, herein incorporated by reference in its entirety.

The above expression is based upon the assumption that all energy delivered to the fluid will arrive at the downstream thermistor as shown in FIG. 3. It should also be recognized that an important feature of the present invention is the ability to arbitrarily confine the electromagnetic radiation to the fluid. In the preferred embodiment of the present invention, the excitation function is a series of pulses, allowing signal averaging of resultant temperature readings to decrease the sensitivity to noise in proportion to the number of pulses. Another excitation function that can be applied to the energy source by the flow estimator 118 is a pseudorandom function as described in U.S. Pat. No. 4,507,974 to Yeldermann, herein incorporated by reference in its entirety. This function makes the temperature measurement relatively insensitive to noise when the sensor output is correlated with the excitation function. However, as one skilled in the art would find apparent, other constant or arbitrary excitation functions may be used depending upon the environment in which the present invention is implemented. For example, the excitation function may be a step function, a sinusoidal function, etc. It can have temporal characteristics that will reduce the sensitivity of the resulting flow calculation to the sources of noise or artifacts that are present, or it can be any arbitrary function of time that results in a reliable measurement of flow.

By using volumetric heating, the present invention can deliver approximately 30 to 60 watts of power to the blood, significantly greater than the power that can be achieved by prior heating methods. If this were continuously dissipated, it would add 30% to the total power generated by metabolism. We therefore use a measurement protocol of intermittent energy deposition to reduce the heat load while maintaining the improved signal-to-noise ratio. Using such protocols allows for temperature measurements to be taken approximately once per minute, which is essentially continuous to a clinician. This approach is more continuous than the saline injection method, wherein saline injections must be periodically administered and measurements must be taken over the course of approximately one hour to obtain a single reading.

Figure 5:
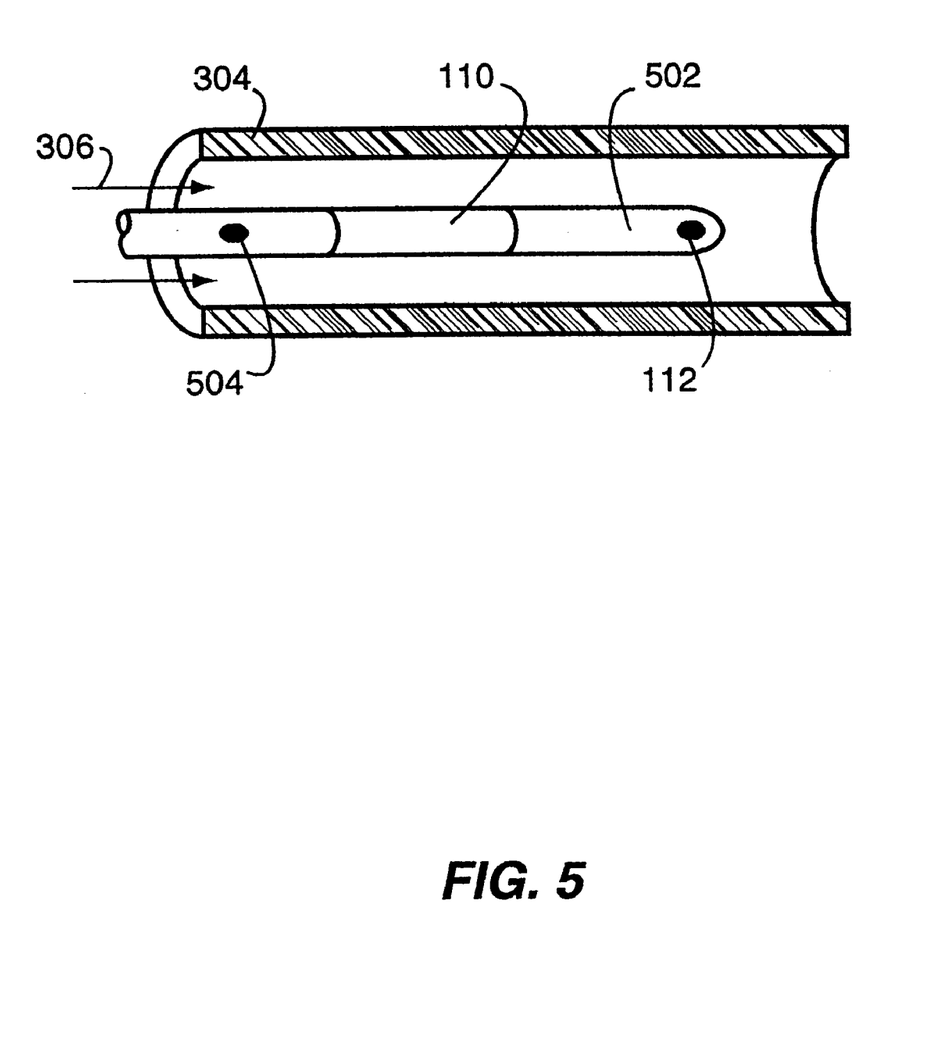
FIG. 5 is a perspective view of an alternative embodiment of the catheter of the present invention having two thermally sensitive elements.

FIG. 5 illustrates an alternative embodiment of the present invention wherein a catheter 502 includes a second thermally sensitive element 504 located upstream from the emitter 110. This second temperature sensitive element 504 is used to monitor the baseline temperature of the fluid 306. This will allow the flow estimator 118 to adjust for drift in the fluid temperature, and will obviate the need to routinely cycle the application laser power q(t) to check for temperature drift. As would be apparent to those skilled in the art, other methods for accounting for baseline temperature drift, such as applying the power in a sinusoidal temporal function and correlating the temperature response to that function, may be implemented.

Figure 6:
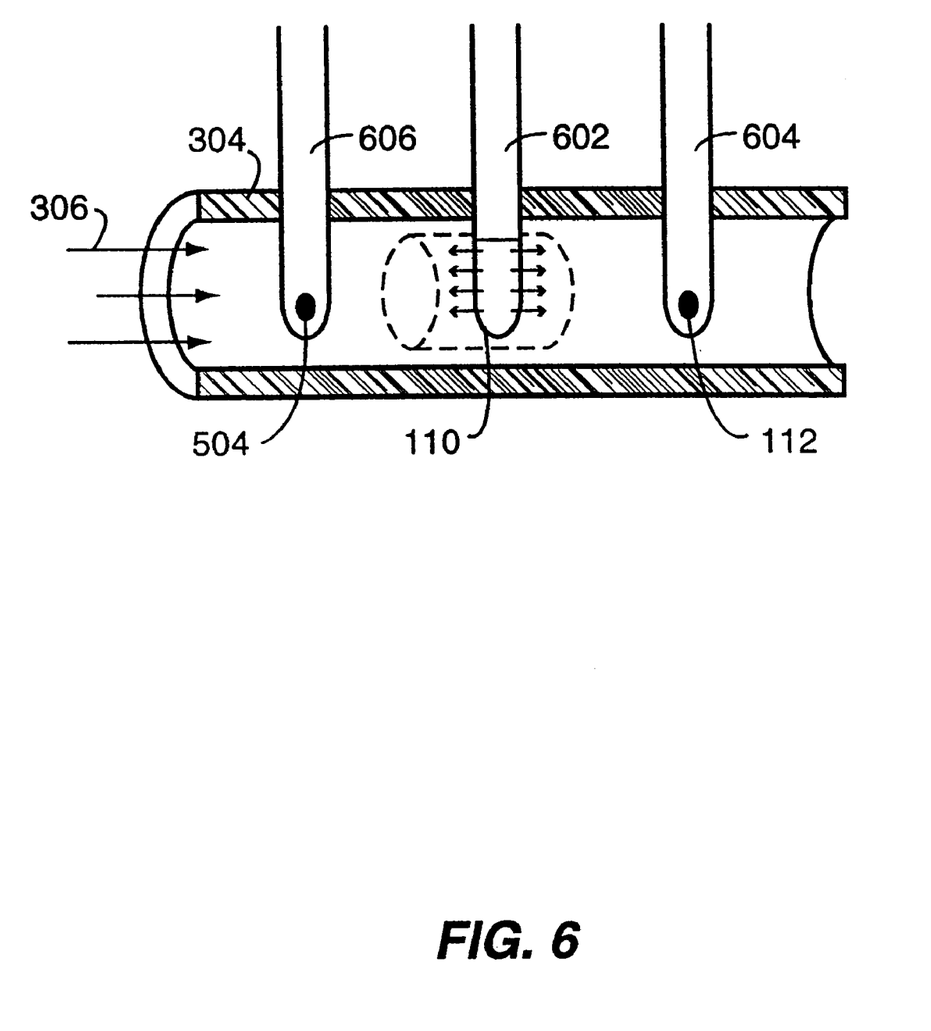
FIG. 6 is a perspective view of an alternative embodiment of the present invention implemented with multiple elongated members.

FIG. 6 illustrates an alternative embodiment of the present invention wherein each temperature sensitive element and the emitter are carried on a separate support member. The emitter 110, temperature sensitive element 112, and temperature sensitive element 504 are introduced into the flowing fluid 306 through the sides of tube 304 using members 602, 604, and 606, respectively.

In an alternative embodiment of the present invention, acoustic-based heating of the blood is performed. In such an embodiment, emitter 110 is an ultrasonic transducer and the laser source is replaced by a high-frequency electrical source connected to emitter 110 via electrical cables 108. The ultrasound transducer converts electrical energy to vibrational energy (ultrasound).

As with the laser source, the frequency of the ultrasound should be such that the ultrasound energy emitting from the transducer will be essentially wholly absorbed within the fluid, with essentially no transmitted energy entering into or through the walls of the tube into which the elongate member is inserted. All other aspects of this embodiment are similar to the laser embodiment described above.

With an ultrasonic transducer, the high-frequency electrical source is preferably a source of electrical energy having a voltage that oscillates in the range of 1 MHz to 100 MHz. The transducer is preferably constructed of lead zirconate titanate (PZT) due to its high transmission efficiency, and formed into a cylindrical shape for uniformly emitting ultrasound radiation in the radial direction. However, as one skilled in the art would find apparent, any commercially available ultrasound transducer now or later developed may be used.

In another embodiment, the electromagnetic energy source is a source of electromagnetic energy in the microwave domain, with emitter 110 being a microwave antenna. Emitter 110 may be any commercially catheter-based microwave antenna now or later developed that will ensure that the microwave energy is emitted in a uniform manner. For example, the emitter may be a dipole, helix, or a spring-type catheter-based antenna. However, other microwave antenna configurations are anticipated.

The microwave energy source comprises a standard medium-power microwave circuit capable of delivering microwave energy in the 433 MHz to 10 GHz range, although other frequencies may be used, depending upon the liquid to be heated and the dimmensions of the area in which heating takes place. The impedance of the source should be matched to the antenna applicator to ensure the most efficient coupling of the microwave energy to the blood.

The present invention may be implemented in a dedicated catheter as described above or, alternatively, may be implemented in a device that performs other cardiac measurement functions as well. For example, the catheter of the present invention may be implemented in a multifunctional device. It may include, for example, a balloon and pressure port. Additional channels may also be included to perform any additional measurements or interventions as desired.

Those familiar with the art will recognize that these embodiments can be used in any fluid where an appropriate source of light, ultrasound or microwave energy can be found that will ensure the energy emitted from the source is essentially wholly absorbed within the fluid and is essentially not transmitted into or through the walls of the surrounding tube or vessel. This invention will be especially useful when applied to the measurement of flowing blood, either through the heart, in one of the arteries emerging from heart, or in an isolated artery or vein. In any application, it should be noted that there will not be any bifurcations in the flow system between the emitter 110 and the temperature measuring device 112; that is, a single-input, single-output system. Furthermore, the frequency range would be different depending on the size of the artery. For example, in the coronary artery, which is approximately a few millimeters in diameter, the extinction length would be in the order of less than one millimeter. Thus, a wavelength of less than 800 namometers may be appropriate.

Preferably, the central flow estimator 118, laser source 104, and temperature sensing unit 114 may physically packaged within one integrated system illustrated by dashed box 128. Such an arrangement results in a compact, self-contained unit that is suitable for use in a medical environment. Other packaging arrangements are considered to be well known in the art.

As noted, the measured flow rate may be presented by a user interface 126, communicating with the central flow estimator 118 through communication path 124. The user interface 126 presentation can be a numerical presentation, a graph of the temporal history of flow, or a report displayed on a computer interface, plotted on paper, or written to a file on disk. Further, it can be interfaced with, or consist solely of, alarms indicated excessive or inadequate flow levels, or it can consist of a variety of other presentations known to those skilled in the art.

To ensure that the catheter tip remains several millimeters from the endocardial wall, alternative embodiments may include umbrella-like extension arms attached just proximal to the tip. The arms will maintain the diffuser at a known distance from the heart wall. The arms will be placed such that they do not interfere with or absorb the laser radiation. Alternatively, radio-opaque markers can be placed on the catheter near the emitter. These markers will indicate the placement of the catheter on X-ray or fluoroscopic images, and will allow the clinician an opportunity to ensure proper placement.

Furthermore, the terms and expressions which have been employed are used as terms of description and not of limitation, and there is no intention, in the use of such terms and expressions, of excluding any equivalents of the features shown and described or portions thereof, but it is recognized that various modifications are possible within the scope of the invention

What is claimed is:

1. A cardiac output measurement system, comprising:

a catheter adapted to be inserted through an atrium of a heart;

an emitter disposed in said catheter for emitting radiation to volumetrically heat a definable volume of blood that passes through said atrium, said radiation being absorbed by the blood and converted into heat;

a temperature sensitive element disposed downstream from said emitter for generating a signal corresponding to the temperature of the blood downstream from said emitter; and control means for controlling the application of said radiation.

2. The system of claim 1, wherein said temperature sensitive element is wholly disposed within said catheter.

3. The system of claim 1, further comprising:

a second catheter, wherein said temperature sensitive element is disposed within said second catheter.

4. The system of claim 1 wherein said control means comprises:

a temperature measurement system coupled to said temperature sensitive element for generating a temperature profile of blood based on the signal received from said temperature sensitive element; and a flow estimator coupled to said temperature measurement system for estimating the flow of blood.

5. The system of claim 1 including an energy source generating electrical energy in the frequency range of 1 MHz to 100MHz, and wherein said emitter comprises a transducer capable of converting said electrical energy to vibrational energy and acoustically radiating said vibrational energy within said volume of blood.

6. The system of claim 1 wherein said catheter further comprises a second temperature sensitive element disposed upstream from said emitter for generating a signal corresponding to the temperature of the blood upstream from said emitter.

7. The system of claim 1 including an energy source for generating electromagnetic radiation; and wherein said emitter comprises an electromagnetic diffuser capable of distributing the electromagnetic radiation substantially uniformly across the length and around circumference of said diffuser.

8. The system of claim 7, wherein said electromagnetic radiation is ultraviolet light having a wavelength in the range of $1\times10^8$ to $4\times10^{-7}$ meters.

9. The system of claim 7, where the electromagnetic radiation is visible light having a wavelength in the range of $4\times10^{-7}$ to $7\times10^{-7}$ meters.

10. The system of claim 7 wherein the electromagnetic radiation is infrared light having a wavelength in the range of $7\times10^{-7}$ to $1\times10^{-3}$ meters.

11. The system of claim 7 wherein said electromagnetic radiation has a microwave frequency in the range of $1\times10^8$ to $3\times10^{11}$ Hz.

12. A catheter for use in a cardiac measurement system having an energy source, comprising:

an elongated member configured to be inserted through an atrium of the heart;

an emitter disposed in said member and using energy from said source to emit radiation to volumetrically heat a definable volume of blood that passes through said atrium, said radiation being absorbed by the blood and converted into heat; and a temperature sensitive element disposed in said member downstream from said emitter for generating a signal corresponding to the temperature of the blood downstream from said emitter.

13. The catheter of claim 12 wherein said temperature sensitive element is disposed within the distal end of said catheter and wherein said emitter is disposed within a portion of said catheter at a position relative to said temperature sensitive element such that said emitter is located within said right atrium when said temperature sensitive element is located within the pulmonary artery.

14. The catheter of claim 17 wherein said electromagnetic radiation has a microwave frequency in the range of $1\times10^8$ to $3\times10^{11}$ Hz.

15. The system of claim 12 wherein said energy source generates electrical energy in the frequency range of 1 MHz to 100 MHz, and said emitter comprises a transducer capable of converting said electrical energy to vibrational energy and acoustically radiating said vibrational energy within said volume of blood.

16. The system of claim 12 wherein said catheter further comprises a second temperature sensitive element disposed upstream from said emitter for generating a signal corresponding to the temperature of the blood upstream from said emitter.

17. The catheter of claim 12 wherein said energy source generates electromagnetic radiation; and said emitter comprises an electromagnetic diffuser capable of distributing the electromagnetic radiation substantially uniformly across the length and around circumference of said diffuser.

18. The catheter of claim 17, wherein said electromagnetic radiation is ultraviolet light having a wavelength in a range of $1\times10^{-8}$ to $4\times10^{-7}$ meters.

19. The catheter of claim 17, where the electromagnetic radiation is visible light having a wavelength in the range of $4\times10^{-7}$ to $7\times10^{-7}$ meters.

20. The catheter of claim 17, wherein the electromagnetic radiation is infrared light having a wavelength in the range of $7\times10^{-7}$ to $1\times10^{-3}$ meters.

21. An apparatus for measuring fluid flow rate in a passageway, comprising:

an elongated member adapted to be inserted into flowing fluid;

an emitter, coupled to said elongated member, for emitting radiation to volumetrically heat a definable volume of flowing fluid, said radiation being absorbed by the flowing fluid and converted into heat;

a temperature sensitive element, located downstream from said emitting means, for generating a signal corresponding to the temperature of the flowing fluid downstream from said emitting means; and control means for controlling the application of said radiation.

22. The apparatus of claim 21 including an energy source generating electrical energy in the frequency range of 1 MHz to 100 MHz, and wherein said emitter comprises a transducer capable of converting said electrical energy to vibrational energy and acoustically radiating said vibrational energy within said volume of flowing fluid.

23. The system of claim 21 wherein said apparatus further comprises a second temperature sensitive element disposed upstream from said emitter for generating a signal corresponding to the temperature of the blood upstream from said emitter.

24. The apparatus of claim 21 including an energy source for generating electromagnetic radiation; and wherein said emitter comprises an electromagnetic diffuser capable of distributing the electromagnetic radiation substantially uniformly across the length and around circumference of said diffuser.

25. The apparatus of claim 24, wherein said electromagnetic radiation is ultraviolet light having a wavelength in a range of $1 \times 10^{-8}$ to $4 \times 10^{-7}$ meters.

26. The apparatus of claim 24, where the electromagnetic radiation is visible light having a wavelength in the range of $4 \times 10^{-7}$ to $7 \times 10^{-7}$ meters.

27. The apparatus of claim 24, wherein the electromagnetic radiation is infrared light having a wavelength in the range of $7 \times 10^{-7}$ to $1 \times 10^{-3}$.

28. The apparatus of claim 24 wherein said electromagnetic radiation has a microwave frequency in the range of $1 \times 10^3$ to $3 \times 10^{11}$ Hz.

29. A method of measuring the volumetric flow rate of a fluid flowing from an upstream location towards a downstream location, comprising the steps of:

(1) inserting an elongated member into flowing fluid;

(2) sensing the baseline temperature of the flowing fluid;

(3) emitting, from an emitter coupled to said member, radiation to volumetrically heat a definable volume of flowing fluid, said radiation being absorbed by the flowing fluid and converted into heat;

(4) sensing the temperature of the flowing fluid downstream from said emitter;

(5) determining a volumetric flow rate of the flowing fluid in accordance with said temperatures and said emitted radiation.

30. The method of claim 29 wherein said baseline temperature of the flowing fluid is measured whenever said emitting radiation is zero.

31. The method of claim 29 wherein said baseline temperature of the flowing fluid is measured upstream from said emitter.

32. The method of claim 29 wherein said radiation is generated by a source of electromagnetic radiation having a wavelength in the ultraviolet light range of $1 \times 10^{-8}$ to $4 \times 10^{-7}$ meters and wherein said emitter comprises an electromagnetic diffuser capable of distributing said electromagnetic radiation substantially uniformly across the length and around circumference of said diffuser.

33. The method of claim 29 wherein said radiation is generated by a source of electromagnetic radiation having a wavelength in the visible light range of $4 \times 10^{-7}$ to $7 \times 10^{-7}$ meters and wherein said emitter comprises an electromagnetic diffuser capable of distributing said electromagnetic radiation substantially uniformly across the length and around circumference of said diffuser.

34. The method of claim 29 wherein said radiation is generated by a source of electromagnetic radiation having a wavelength in the infrared light range of $7 \times 10^{-7}$ to $1 \times 10^{-3}$ meters and wherein said emitter comprises an electromagnetic diffuser capable of distributing said electromagnetic radiation substantially uniformly across the length and around circumference of said diffuser.

35. The method of claim 29 wherein said radiation is generated by a source of electromagnetic radiation having a microwave frequency in the range from $1 \times 10^8$ to $3 \times 10^{11}$ Hz, and wherein said emitter comprises a microwave antenna capable of distributing said microwave radiation substantially uniformly across the length and around circumference of said diffuser.

36. The method of claim 29 wherein said radiation is generated by a source of electrical energy in the frequency range of 1 MHz to 100 MHz, and wherein said emitter comprises a transducer capable of converting said electrical energy to vibrational energy and acoustically radiating said vibrational energy within said volume of flowing fluid.

37. The method of claim 29, wherein said volumetric flow rate, in units of m³/sec, is estimated by said central flow estimator using the relationship:

$$\text{Flow} = \frac{\int_0^{\tau_2} q(t) dt}{\rho_f c_f \int_{t_3}^{t_4} (T(t) - T_{Baseline}) dt}$$

wherein q(t) is the applied heat (Watts), $\varrho_f$ is the density of the blood (Kg/m³), $c_1$ is the specific heat of the blood (Joules/Kg °K), T(t) is the measured temperature at time t (°K), and $T_{Baseline}$ is the baseline temperature (°K).

* * * * *